(12) United States Patent
Fujinami (10) Patent No.: US 7,125,631 B2
(45) Date of Patent: Oct. 24, 2006

(54) LITHIUM SALT, IONIC CONDUCTOR AND LIQUID ELECTROLYTE

(75) Inventor: Tatsuo Fujinami, Hamamatsu (JP)

(73) Assignees: Toyota Jidosha Kabushiki Kaisha, Toyota (JP); Genesis Research Institute, Inc., Nagoya (JP)

( * ) Notice: Subject to any disclaimer, the term of this patent is extended or adjusted under 35 U.S.C. 154(b) by 428 days.

(21) Appl. No.: 10/290,201

(22) Filed: Nov. 8, 2002

(65) Prior Publication Data
US 2003/0108798 A1    Jun. 12, 2003

(30) Foreign Application Priority Data
Nov. 9, 2001   (JP)   ............... 2001-344886

(51) Int. Cl.
*H01M 6/18* (2006.01)

(52) U.S. Cl. ............... 429/306; 429/317; 429/316; 429/338; 429/337; 429/341; 556/170; 556/176

(58) Field of Classification Search ............... 429/306, 429/317, 316, 337, 338, 341; 556/170, 176
See application file for complete search history.

(56) References Cited

U.S. PATENT DOCUMENTS

| | | | | |
|---|---|---|---|---|
| 5,597,663 A * | 1/1997 | Pendalwar et al. | ......... | 428/188 |
| 6,114,070 A * | 9/2000 | Yoshida et al. | ............. | 429/332 |
| 6,392,076 B1 * | 5/2002 | Strauss et al. | ............... | 524/176 |
| 6,441,942 B1 * | 8/2002 | Branz et al. | ................ | 359/265 |
| 2004/0266981 A1 * | 12/2004 | Yokoyama et al. | ......... | 528/394 |

FOREIGN PATENT DOCUMENTS

| | | | |
|---|---|---|---|
| JP | 2001143764 | * | 5/2001 |
| JP | 2001-210332 | * | 8/2001 |

OTHER PUBLICATIONS

Fujinami et al. "New Inorganic-Organic Hybrid Li+ Ion Conducting Polymer Electrolytes" Chemistry Letters (1998), (7), pp. 619-620.*

Cerny et al. "Alkoxohydridoaluminates: multinuclear NMR study of sodium hydrido-(2-methoxyethoxo)aluminates" Journal of Organometallic Chemistry 516 (1996), pp. 115-122.*

Tatsuo Fujinami et al., "Ion Conducting Polymers Containing the Ate-Complex Structure," Sep. 5, 1996, pp. 30-37, Department of Materials Science, Faculty of Engineering, Shizuoka University, Japan (with English-language abstract and Partial English-language translation).

Fujinami et al, "Molecular design of inorganic-organic hybrid polyelectrolytes to enhance lithium ion conductivity", *Electrochimica Acta*, vol. 45, pp. 1181-1186, 2000.

Fujinami et al, "New Inorganic-Organic Hybrid Li+ Ion Conducting Polymer Electrolytes", *Chemistry Letters*, pp. 619-620, 1998.

Fujinami et al, "Siloxyaluminate Polymers with High Li+ Ion Conductivity", *Chemistry of Materials*, vol. 9, No. 10, pp. 2236-2239, 1997.

Onishi et al, "Synthesis of Aluminate Polymer Complexes as Single-Ionic Solid Electrolytes", *Chemistry of Materials*, vol. 8, pp. 469-471, 1996.

Rawsky et al, "Aluminosilicate/Poly(ethylene glycol) Copolymers: A New Class of Polyelectrolytes", *Chemistry of Materials*, vol. 6, pp. 2208-2209, 1994.

Doan et al, "Synthesis and Electrical Response of Single-Ion Conducting Network Polymers Based on Sodium Poly(tetraalkoxyaluminates)", *Chemistry of Materials*, vol. 3, pp. 418-423, 1991.

Mehta et al, "Novel inorganic-organic polymer electrolytes—preparation and properties", *Solid State Ionics* 113-115, pp. 187-192, 1998).

* cited by examiner

*Primary Examiner*—Laura Weiner
(74) *Attorney, Agent, or Firm*—Buchanan Ingersoll & Rooney PC (57) ABSTRACT

Disclosed are a lithium salt expressed by a formula, $LiAlX_n(OY)_{4-n}$, where "X" is an electrophilic substituent group and "Y" is an oligoether group, an ionic conductor with the lithium salt dispersed in a structural member, and a liquid electrolyte with the lithium salt dissolved in a solvent. For example, the ionic conductor exhibits high ionic conductivity as well as high lithium ion transport number.

12 Claims, 5 Drawing Sheets

LITHIUM SALT, IONIC CONDUCTOR AND LIQUID ELECTROLYTE

BACKGROUND OF THE INVENTION

1. Field of the Invention

The present invention relates to a lithium salt, an ionic conductor and a liquid electrolyte which can be used for polymer solid electrolytes and liquid electrolytes of lithium secondary batteries.

2. Description of the Related Art

Since lithium salts, which have been used for electrolytes of lithium secondary batteries conventionally, are solids which have a chemical structure of high dissociation, they do not exhibit ionic conduction independently. Hence, in order to give them ionic conduction, they have been conventionally dissolved in appropriate solvents to use.

Incidentally, from the viewpoint of inhibiting reactions with electrode active materials, nonaqueous solvents have been used in general for solvents in which lithium salts are dissolved. Ordinary nonaqueous solvents are combustible. Accordingly, in lithium secondary batteries which are expected to be applied to consumer appliances, nothing can be better than to avoid using such nonaqueous solvents if possible at all.

Hence, in order to keep nonaqueous solvents from using, it has been carried out forming solid electrolytes by dissolving lithium salts in appropriate polymers. Currently, as solid electrolytes having been reported so far, systems have been investigated in which alkali metals of good dissociation are dissolved in ether-based polymers, being cationic conductors. Since solid electrolytes are of high safety, in addition, since they are good in terms of formability to film, light-weightness, flexibility, and elasticity, they are expected to be more promising in the future.

However, although sold electrolytes, in which lithium salts are dissolved in appropriate polymers, exhibit high ionic conductivities, they exhibit lithium ion transport number of 0.5 or less. In particular, they exhibit much lower lithium ion transport number in polyether. Moreover, when conventional lithium salts are dissolved in solid electrolytes, not only cations move well, but also anions move well. Accordingly, the deposition of cations onto cathode takes place so that there arises a problem in that the ionic conductivity lowers. It is believed that the problem could be solved by restricting the movement of cations, specifically by employing single ionic conductors, in which cations move preferentially, as the lithium salt. However, since single ionic conductors fasten paired anions, the conduction of cations has been restricted as well so that the ionic conductivities lower.

Moreover, molten lithium salts have been known which turn into liquid at room temperature independently. However, the conducting species is anions, not cations. In addition, the present inventors reported a polymer electrolyte which has an aluminate structure. However, not only the method of synthesizing the polymer electrolyte has been complicated, but also the ionic conductivity has not been sufficiently high.

SUMMARY OF THE INVENTION

Hence, it is an object of the present invention to provide a lithium salt of high safety, lithium salt which exhibit high lithium ion conduction at room temperature independently without using a nonaqueous solvent, and an ionic conductor making a solid electrolyte whose ionic conductivity as well as lithium ion transport number are high simultaneously.

It is a further object of the present invention to provide a liquid electrolyte in which a lithium salt is dissolved in a solvent as conventional ones, but which exhibits good ionic conductivity.

In order to achieve the aforementioned objects, the present inventors studied lithium salts, the systems of ionic conductors, and liquid electrolytes diligently. As a result, they discovered the following. Namely, in single ionic conductors, when ion paring is effected too strongly between cations and anions, the mobility of cations lowers. Accordingly, they discovered that, in addition to lowering the mobility of anions, it is important to lower ion paring between cations and anions.

The present inventors paid attention to aluminate complexes. In order to lower ion pairing, they thought of introducing electrophilic substituent groups into aluminate complexes so that the charge density of anions was lowered so as to lower the interaction of anions and cations. Moreover, they thought of making it possible to form an ion conducting pathway in aluminate complexes themselves and simultaneously to lower the mobility of anions by introducing oligoether chains into aluminate complexes appropriately.

Based on the above discoveries, the present inventors invented a lithium salt expressed by a formula below:

$LiAlX_n(OY)_{4-n}$, where "X" is an electrophilic substituent group and "Y" is an oligoether group.

It is possible to turn the lithium salt into liquid state at room temperature. The present inventors confirmed that only the lithium salt per se exhibited high ionic conductivity.

Then, by dispersing the lithium salt in appropriate structural members, it was possible to obtain ionic conductors making solid electrolytes whose ionic conductivity as well as lithium ion transport number were high simultaneously.

Moreover, by dissolving the lithium salt in appropriate solvents, it was possible to obtain liquid electrolytes which exhibited high ionic conduction.

As having described so far, when the lithium salt, comprising an aluminate structure having an oligoether group, is applied to ionic conductors (or solid electrolytes), the resulting ionic conductors exhibit high ionic conductivity and lithium ion transport number. Further, by controlling the molecular weight of oligoether group, it is possible to freely change the lithium salt from solid to liquid. Furthermore, due to the presence of oligoether group, the movement of anions is restricted so that it is possible to establish the single ion movement of cations.

Moreover, when an electrophilic substituent group is introduced into the lithium salt comprising an aluminate structure, it is possible to provide a lithium salt which is suitable for liquid electrolytes.

In addition, when an oligoether group and an electrophilic substituent group are introduced into the lithium salt comprising an aluminate structure, it is possible to further optimize the characteristics as single ionic conductor, characteristics which result from the oligoether group, by ionpairing lowering effect due to the electrophilic substituent group.

Thus, the ionic conductor and liquid electrolyte, using such a good lithium salt according to the present invention, exhibit good ionic conduction characteristics.

BRIEF DESCRIPTION OF THE DRAWINGS

A more complete appreciation of the present invention and many of its advantages will be readily obtained as the same becomes better understood by reference to the following detailed description when considered in connection with the accompanying drawings and detailed specification, all of which forms a part of the disclosure.

DETAILED DESCRIPTION OF THE PREFERRED EMBODIMENTS

Having generally described the present invention, a further understanding can be obtained by reference to the specific preferred embodiments which are provided herein for the purpose of illustration only and not intended to limit the scope of the appended claims.

Lithium Salt

The lithium salt according to the present invention is expressed by a formula below:

$LiAlX_n(OY)_{4-n}$, where "X" is an electrophilic substituent group and "Y" is an oligoether group.

Here, the value "n" falls in a range of from 0 to 4. When the value "n" is 1 or more, the action of the electrophilic substituent group "X" is effected so well that the ionic conduction of the present lithium salt is enhanced. In particular, when the value "n" is 2, the characteristics of the present lithium salt, such as the ionic conduction, become very favorable. Moreover, a plurality of the present lithium salts whose value "n" differs with each other can be made into a mixture to use.

In the formula, "X" is an electrophilic substituent group. As for "X," it is possible to exemplify —F; —CN; $RCO_2$—, $RSO_3$—, and $(RSO_2)_2N$—, where "R" is an alkyl group, a perfluoroalkyl group, a phenyl group, or a pentafluorophenyl group; or a pentafluorphenoxy group. In particular, "X" can preferably be at least one member selected from the group consisting of $RCO_2$—, $RSO_3$—, and $(RSO_2)_2N$—, where "R" is at least one member selected from the group consisting of an alkyl group and a perfluoroalkly group. Moreover, "X" can further preferably be $RCO_2$—, where "R" is at least one member selected from the group consisting of an alkyl group and a perfluoroalkyl group.

In the formula, "Y" is an oligoether group. For example, it is possible to exemplify an oligoalkyleneoxide group expressed by a general formula: $R'(OR'')_m$—, where R' and R'' are a hydrocarbon group whose number of carbon atoms falls in a range of from 1 to 8, respectively, and "m"$\geq$1. In particular, $CH_3(OCH_2CH_2)_m$—, where "m"$\geq$1, can be an especially preferable option. Due to the characteristics of "Y," such as the molecular weight, the properties or states of the present lithium salt vary greatly. Specifically, when the molecular weight of "Y," being an oligoether group, the characteristics of the oligoether group are dominant in the present lithium salt so that the present lithium salt changes from solid to liquid. From the viewpoint of ionic conduction, the present lithium salt can preferably be liquid at room temperature. Moreover, by enlarging the molecular weight of "Y," the viscosity is enlarged when the present lithium salt is made into a later-described liquid electrolyte.

Specifically, the molecular weight of "Y" can preferably fall in a range of from 150 to 540 approximately. In particular, when "Y" is $CH_3(OCH_2CH_2)_m$—, the value "m" can preferably fall in a range of from 3 to 11.8 approximately. In particular, when the value "m" falls in a range of from 5 to 9, it is preferable because the oligoether group gives ionic conduction to the present lithium salt very well.

Moreover, when the present lithium salt is used independently, from the viewpoint of ionic conductivity, it is possible to set the number of oxygen atoms, resulting from "Y" in the formula, so that a ratio (O/Li) of the number of oxygen atoms with respect to the number of lithium ions can preferably fall in a range of from 2/1 to 90/1, further preferably from 6/1 to 30/1, furthermore preferably from 10/1 to 18/1.

The process for preparing the present lithium salt is not limited in particular. However, it is possible to synthesize it by the following process, for example. LiAlH$_4$ is mixed and reacted with a hydroxide derivative (YOH) of a corresponding oligoether group "Y" in an appropriate solvent. The reaction product is mixed and reacted with a hydroxide derivative (XOH) of a corresponding electrophilic substituent group "X" in an appropriate solvent.

Then, the present lithium salt can be prepared by refining the reaction product with an appropriate method. It is possible to adjust the value "n" in the formula by varying the reaction conditions, such as the mixing ratio of LiAlH$_4$ and YOH. Note that, in order to control side reactions, it is preferable to-carry out the above reactions at a low temperature, for example, at 0° C. or less, or at the dry ice temperature (i.e., −78.5° C.) or less.

Ionic Conductor

An ion conductor according to the present invention comprises a structural member, and the above-described lithium salt dispersed in the structural member. From the viewpoint of the ionic conductivity, it is possible to set the mixing ratio of the lithium salt and the structural member or the oxygen content in "Y" of the lithium salt so that a ratio (O/Li) of the sum of the number of oxygen atoms, resulting from "Y" in the formula, and ethereal oxygen atoms, included the structural member, with respect to the number of lithium ions, included in the lithium salt, can fall in a range of from 6/1 to 100/1, further preferably from 12/1 to 30/1, furthermore preferably from 16/1 to 24/1. Specifically, the present ionic conductor can comprise the present lithium salt in an amount of from 20 to 95% by mass, preferably from 40 to 90% by mass, furthermore preferably from 70 to 90% by mass, and the balance of the structural member.

The structural membercan preferably be at least one member selected from the group consisting of polyethylene oxide (PEO), ethylene oxide-propylene oxide copolymers (EO-PO), poly(methoxyoligoethyleneglycoxy) methacrylate, polymethyl methacrylate (PMMA), polyethyl methacrylate, polybutyl methacrylate, polyvinylidene fluoride (PVdF), and vinylidene fluoride-hexafluoropropylene copolymers (PVdF-HFP). These compounds are preferable options because they are good in terms of the ionic conduction and are simultaneously good in terms of the film-forming ability. Thus, they are suitable as a raw material for solid electrolytes of lithium secondary batteries. In particular, a polyether-based polymer, for example, PEO is a preferable option.

The lithium salt, included in the present ionic conductor, is the above-described present lithium salt. Accordingly, it will not be described in detail herein.

Moreover, the present ionic conductor can further include a filler. As for the filler, barium titanate is a suitable option. Barium titanate can improve the strength of the present ionic conductor. In addition, not only barium titanate can keep the reduction of ionic conduction minimum when it is compounded in an appropriate amount, for example, in an amount of from 2 to 15% by mass, but also it can improve the ionic conductivity when it is compounded in an amount of from 5 to 10% by mass. As a whole, the present ionic conductor can comprise the present lithium salt in an amount of from 10 to 90% by mass, and preferably from 50 to 80% by mass, the filler in an amount of from 2 to 20% by mass, preferably from 2 to 15% by mass, furthermore preferably from 5 to 10% by mass, and the balance of the structural member.

It is possible to prepare the present ionic conductor in the following manner. The structural member and the lithium salt can be dissolved and stirred in an appropriate solvent, and thereafter the solvent can be removed to prepare the present ionic conductor. Alternatively, the structural member and the lithium salt can be kneaded under appropriate conditions, such as heating, by a kneader, and the lithium salt can be dispersed in the structural member to prepare the present ionic conductor.

Liquid Electrolyte

A liquid electrolyte according to the present invention comprises a solvent, and the above-described lithium salt dissolved in the solvent. Specifically, the present liquid electrolyte can comprise the present lithium salt in an amount of from 1 to 40% by mass, preferably from 2 to 30% by mass, furthermore preferably from 5 to 20% by mass, and the balance of the solvent.

As for the solvent, it is possible to use solvents which have been used usually in nonaqueous electrolyte secondary batteries. For example, the solvent can preferably be at least one member selected from the group consisting of ethylene carbonate (EC), propylene carbonate (PC), diethyl carbonate (DEC), dimethyl carbonate, γ-butyrolactone, diethylene glycol dimethylether, and ethylene glycol dimethylether.

The lithium salt, included in the present liquid electrolyte, is the above-described present lithium salt. Accordingly, it will not be described in detail herein.

EXAMPLES

Example No. 1

Preparation of Lithium Salt

1M LiAlH$_4$ was dissolved in 5 mL tetrahydrofuran (THF) to prepare a first THF solution. 0.551 g (3.36 mmol) triethylene glycohol monomethylether (TEGMME) was dissolved in 5 mL THF to prepare a second THF solution. Then, the second THF solution was dropped slowly to 1.68 mL (1.68 mmol) first THF solution at −78° C. Thereafter, the temperature of the mixture solution was returned slowly to room temperature, and the mixture solution was stirred for 4 hours. Meanwhile, 0.385 g (3.36 mmol) trifluoroacetic acid was dissolved in 5 mL THF to prepare a third THF solution. Next, the reactant solution was dropped slowly to the third THF solution at −78° C. The temperature of the mixture solution was returned slowly to room temperature, and the mixture solution was stirred for 9 hours. The solvent was distilled out by depressurizing, and the reactant was further dried at 70° C. by depressurizing for 48 hours. Thus, a transparent and highly viscous lithium salt was prepared, and was labeled as "SaltA (m=3)." "SaltA (m=3)" was obtained in an amount of 0.981 g, and the yield was 98.0%. Note that "SaltA (m=3)" was a compound expressed by the above-described formula. Specifically, synthesized "SaltA (m=3)" was a compound whose value "n" in the formula was 2, "X" was CF$_3$COO—, and "Y" was an oligoethylene oxide group. Moreover, the value "m" set forth in the parenthesis specifies an average polymerization degree of the ethylene oxide of the oligoethylene oxide group in "Y."

Moreover, "SaltA (m=7.2)" and "SaltA (m=11.8)" were synthesized similarly.

R = CH$_3$(OCH$_2$CH$_2$)$_m$  m = 3, 7.2, 11.8

Measurement on Ionic Conductivity

The ionic conductivities of the respective lithium salts were measured at a plurality of temperatures. The ionic conductivities were measured by means of the alternate-current impedance method in which stainless steel electrodes were used. The cells used for measuring the ionic conductivities were heated at 90° C. in an argon atmosphere for 1 hour, and were thereafter cooled at room temperature for 3 hours to use.

Result

Figure 1:
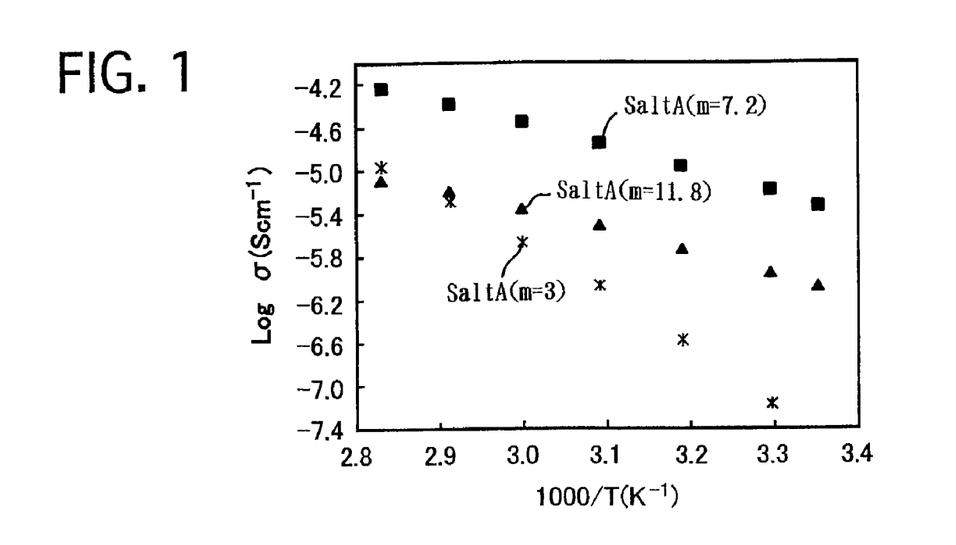
FIG. 1 is a graph for illustrating the temperature dependencies of the ionic conductivities exhibited by respective test samples in Example No. 1.

When "m"=3, the synthesized lithium salt was solid. On the other hand, when "m"=7.2 and "m"=11.8, the synthesized lithium salts were liquid. FIG. 1 illustrates the results of the measurement on the temperature dependencies of the ionic conductivities of the lithium salts. In the drawing, the logarithmic values of the ionic conductivities are plotted to the vertical axis, and the inverses of the temperatures (K) multiplied by a factor of 1,000 are plotted to the horizontal axis. It is apparent from FIG. 1 that, among the three lithium salts, the lithium salt whose "m"=7.2 exhibited the highest ionic conductivities. The reason is believed as follows. When "m"=7.2, the ratio (O/Li) of the number of ethereal oxygen atoms with respect to the number of lithium atoms was 14.4 so that the length of the oligoether chain, which took on moving lithium ions, was optimized.

Example No. 2

Preparation of Ionic Conductors Comprising Polyethylene Oxide (PEO) and "SaltA (m=3)" or "SaltA (m=7.2)

(1) 0.10 g PEO and 0.1646 g "SaltA (m=3)," which was synthesized in Example No. 1, were dissolved in 15 mL acetonitrile. The mixture was stirred for 12 hours. Thereafter, the solvent was distilled out by depressurizing, and the reactant was further dried at 70° C. by depressurizing for 24 hours. Thus, a white ionic conductor was prepared, and was labeled as "PEO+SaltA (m=3)." Note that, in "PEO+SaltA (m=3)," the ratio (O/Li) by number of atoms, i.e., the sum of the number of oxygen atoms, resulting from the oligoethylene oxide group, and ethereal oxygen atoms, included the structural member, with respect to the number of lithium ions, included in the lithium salt, was 20/1. Unless otherwise specified, the ratio (O/Li) will be hereinafter expressed in a ratio by number of atoms.

Moreover, the following were synthesized similarly:
"PEO+SaltA (m=3)" in which the ratio (O/Li) was 16/1;
"PEO+SaltA (m=7.2)" in which the ratio (O/Li) was 20/1;
"PEO+SaltA (m=7.2)" in which the ratio (O/Li) was 24/1; and
"PEO+SaltA (m=7.2)" in which the ratio (O/Li) was 28/1.

Note that, unless otherwise specified, the mixing ratios of lithium salt and PEO were adjusted so as to establish the aimed O/Li ratio values.

(2) Each of "SaltA (m=3)" and "SaltA (m=7.2)" was mixed with PEO to similarly prepare ionic conductors. In this instance, the ratio (O/Li) was fixed at 20/1.

Measurement on Ionic Conductivity

The ionic conductivities of the ionic conductors set forth in (1) and (2) above were measured in the same manner as Example No. 1.

Result

Figure 2:
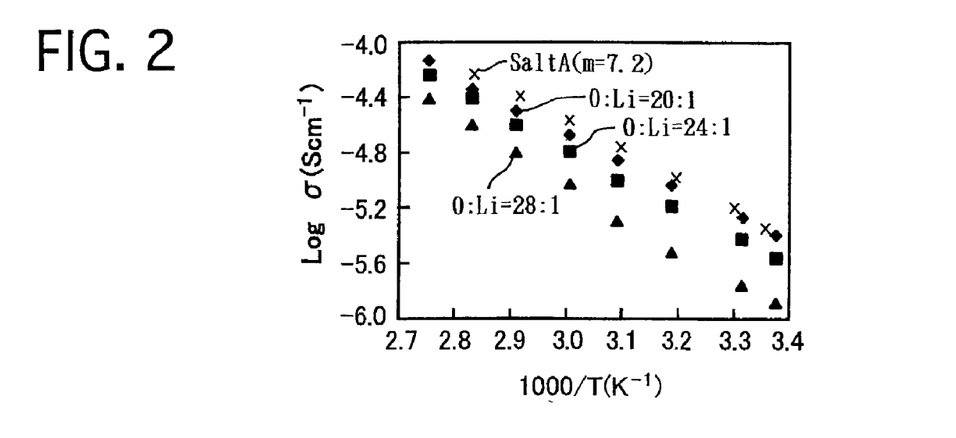
FIG. 2 is a graph for illustrating the temperature dependencies of the ionic conductivities exhibited by respective test samples in Example No. 2.
Figure 3:
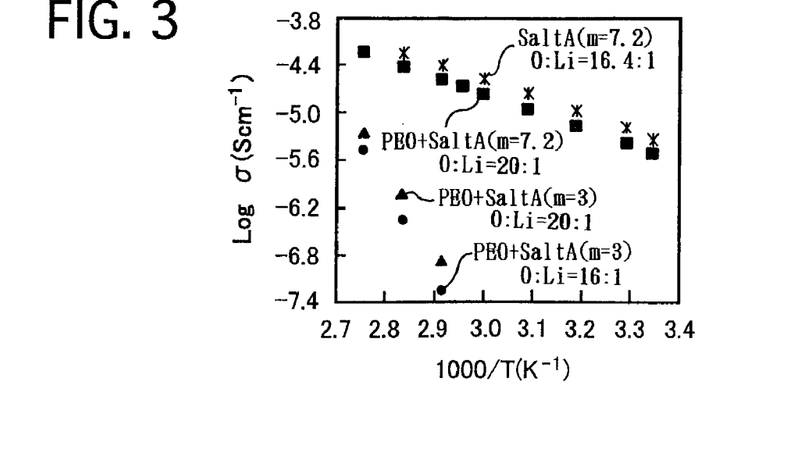
FIG. 3 is a graph for illustrating the temperature dependencies of the ionic conductivities exhibited by respective test samples in Example No. 2.

FIG. 2 illustrates the results of the measurements on the ionic conductors prepared in (1) above. In FIG. 2, there are also illustrated the ionic conductivities of independent "SaltA (m=7.2)" for reference. Moreover, FIG. 3 illustrates the results of the measurements on the ionic conductors prepared in (2) above. In FIG. 3, there are also illustrated the ionic conductivities of independent "SaltA (m=7.2)" and "PEO+SaltA (m=3)" in which the ratio (O/Li) was 16/1, one of the ionic conductors prepared in (1) above.

The following are apparent from FIGS. 2 and 3. As illustrated in FIG. 3, the ionic conductivities of the ionic conductors of "PEO+SaltA" system were higher when the ether chain length of "SaltA" was "m"=7.2 than when it was "m"=3. As illustrated in FIG. 2, the ionic conductivities could be optimized when the ratio (O/Li) was 20/1.

The ionic conductivities of "PEO+SaltA (m=7.2) in which the ratio (O/Li) was 20/1 were relatively high, and were close to the values of independent "SaltA (m=7.2)." Moreover, in the system, the abrupt change of the ionic conductivities, which resulted from melting crystalline region, was not observed. Note that the phenomenon is usually observed in PEO-based electrolytes. Accordingly, it was shown that "SaltA (m=7.2)" possessed the action of plastisizing PEO as well. It is possible to assume that the advantage resulted from the fact that the crystallinity in each of the ionic conductors, "PEO+SaltA (m=3)," "PEO+SaltA (m=7.2)" and "PEO+SaltA (m=11.8)," was 25, 9 and 40%, respectively, and from the fact that the crystallinity of the ionic conductor in which "m"=7.2 was the lowest. Note that the crystallinities were measured by means of the differential scanning calorimetry. Thus, from above, it was verified that "PEO+SaltA (m=7.2)" in which the ratio (O/Li) was 20/1 was a favorable ionic conductor in terms of the film strength as well as the ionic conductivity.

Note that "SaltB (m=3)" and "SaltB (m=7.2)" which did not have any electrophilic substituent group, "SaltC" which did not have any oligoether substituent group, and "SaltD" which had a weak electrophilic substituent group were synthesized in the same manner as Example No. 1, and were dissolved in PEO to prepare ionic conductors. The ionic conductivities of the resulting ionic conductors are not mentioned herein specifically. However, it should be noted that, as a whole, they were lower than those of the ionic conductors of "PEO+SaltA" system.

The specific arrangements of "SaltB," "SaltC" and "SaltD" were as follows:

"SaltB" was expressed by $LiAl(OY)_4$, where "Y" was an ethylene oxide chain whose polymerization degree "m" was 7.2;

"SaltC" was expressed by $LiAlX_4$, where "X" was $-OCOCF_3$; and

"SaltD" was expressed by $LiAlX_2(OY)_2$, where "X" was $-OCOCH_3$ and "Y" was an ethylene oxide chain whose polymerization degree "m" was 7.2.

Moreover, the ionic conductors of "PEO+SaltA" system were stable up to a temperature of 250° C. or more at least. Their potential windows were as high as 4.5 V approximately.

Measurement on Lithium Ion Transfer Number and Result

The $Li^+$ transfer number $T_+$ of one of the ionic conductors, "PEO+SaltA (m=7.2)" in which the ratio (o/Li) was 20/1, was assessed by means of Eq. (b) below in which the AC impedance method and the DC impedance method were combined. The result is set forth in Table 1 below.

$$T_+ = \frac{I_s R_b^f}{I_0 R_b^i}\left(\frac{\Delta V - I_0 R_e^i}{\Delta V - I_s R_e^s}\right) \quad \text{(Eq. (b))}$$

where $T_+$ is lithium ion transfer number; $I_0$ is initial current value; $I_s$ is steady-state current value; $\Delta V$ is applied voltage; $R_e^i$ is initial boundary resistance value; $R_e^s$ is steady-state boundary resistance value; $R_b^i$ is initial bulk resistance value; and $R_b^f$ is terminal bulk resistance value.

TABLE 1

|  | $R_b^i$ (Ω) | $R_e^i$ (Ω) | $I_0$ (A) | Δv | $R_b^f$ (Ω) | $R_e^s$ (Ω) | $I_s$ (A) | $T_+$ |
|---|---|---|---|---|---|---|---|---|
| PEO + SaltA (m = 7.2) | 1.61 × 10$^5$ | 2,526 | 2.25 × 10$^{-7}$ | 0.037 | 2.09 × 10$^5$ | 2.32 × 10$^4$ | 1.23 × 10$^{-7}$ | 0.76 |

It is apparent from Table 1 that the lithium ion transport number of "PEO+SaltA (m=7.2)" was much higher than those of ordinary PEO-based electrolytes whose $T_+$=0.2–0.4 approximately. The reasons are believed as follows. In "PEO+SaltA (m=7.2)," the aninos are so large that they are less likely to diffuse; and, since the ether chains of PEO make pseudo-cross-linkages with the ether chains of "SaltA" by way of the lithium ions, the anions of "SaltA" are inhibited from moving.

Moreover, "PEO+SaltA (m=3)" and "PEO+SaltB" will not be described in detail herein. However, their T+values were 0.49 and 0.19, respectively.

Example No. 3

Preparation of Ionic Conductors Comprising Ethylene Oxide (EO)-Propylene Oxide (PO) Copolymer and "SaltA" and Measurement on Ionic Conductivity 0.0600 g EO-PO, in which EO/PO=90/10 by mol, and 0.3476 g "SaltA (m=7.2)" were dissolved in 15 mL THF. The mixture was stirred for 12 hours. Thereafter, the solvent was distilled out by depressurizing, and the reactant was further dried at 70° C. by depressurizing for 24 hours. Thus, a transparent ionic conductor was prepared, and was labeled as "EO-PO+SaltA (m=7.2)." Note that, in "EO-PO+SaltA (m=7.2)," the ratio (O/Li) by number of atoms, i.e., the sum of the number of oxygen atoms, resulting from the oligoethylene oxide group, and ethereal oxygen atoms, included the structural member, with respect to the number of lithium ions, included in the lithium salt, was 20/1.

Figure 4:
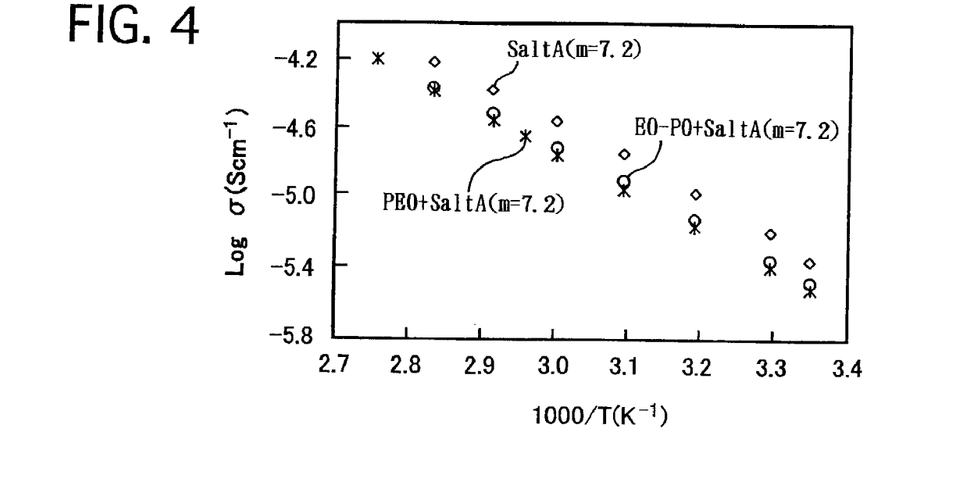
FIG. 4 is a graph for illustrating the temperature dependencies of the ionic conductivities exhibited by respective test samples in Example No. 3.

The ionic conductivities of the ionic conductor of "EO-PO+SaltA (m=7.2)" system in which the ratio (O/Li) was 20/1 were compared with those of "SaltA (m=7.2)" and the ionic conductor of "PEO+SaltA (m=7.2)" system. FIG. 4 illustrates the results.

It is apparent from FIG. 4 that the ionic conductivities of the ionic conductor of "EO-PO+SaltA (m=7.2)" system were very close to those of the ionic conductor of "PEO+SaltA (m=7.2)" system. Moreover, similarly to the ionic conductor of "PEO+SaltA (m=7.2)" system, no abrupt change of the ionic conductivity, resulting from melting crystalline ether chains, was seen. However, the ionic conductor of "PEO+SaltA (m=7.2)" system was better in terms of the film strength than the ionic conductor of "EO-PO+SaltA (m=7.2)" system.

Example No. 4

Preparation of Ionic Conductors Comprising Poylvinylidene Fluoride (PVdF) and "SaltA" and Measurement on Ionic Conductivity 0.211 g PVdF and 0.493 g "SaltA (m=7.2)" were dissolved in 15 mL THF. The mixture was stirred for 12 hours. Thereafter, the solvent was distilled out by depressurizing, and the reactant was further dried at 70° C. by depressurizing for 24 hours. Thus, a white and soft ionic conductor was prepared, and was labeled as "PVdF30+SaltA (m=7.2)." In "PVdF30+SaltA (m=7.2)," PVdF and "SaltA (m=7.2)" were mixed with PVdF:"SaltA (m=7.2)"=30:70 by mass. Moreover, another ionic conductor, "PVdF50+SaltA (m=7.2)," was prepared similarly. In "PVdF50+SaltA (m=7.2)," PVdF and "SaltA (m=7.2)" were mixed with PVdF:"SaltA (m=7.2)"=50:50 by mass.

Figure 5:
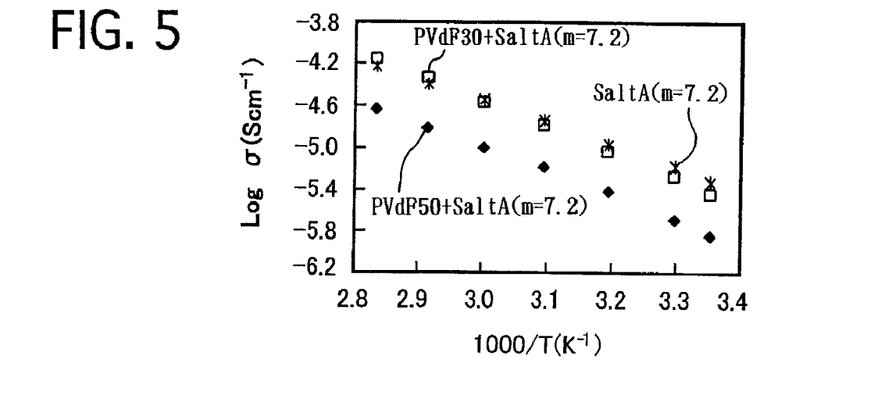
FIG. 5 is a graph for illustrating the temperature dependencies of the ionic conductivities exhibited by respective test samples in Example No. 4.

FIG. 5 illustrates the measurement results of the ionic conductivities. When PVdF was added in an amount of 30% by mass, the ionic conductivities were substantially identical values with those of "SaltA (m=7.2)," but the film strength was not sufficient. When PVdF was added in an amount of 50% by mass, the ionic conductor was improved in terms of the film strength, but it was seen to exhibit lowered ionic conductivities.

Example No. 5

Preparation of Ionic Conductors Comprising Polymethyl Methacrylate (PMMA) and "SaltA" and Measurement on Ionic Conductivity 0.1348 g PMMA and 0.3146 g "SaltA (m=7.2)" were dissolved in 20 mL THF. The mixture was stirred for 12 hours. Thereafter, the solvent was distilled out by depressurizing, and the reactant was further dried at 70° C. by depressurizing for 24 hours. Thus, a transparent ionic conductor was prepared, and was labeled as "PMMA30+SaltA (m=7.2)." In "PMMA30+SaltA (m=7.2)," PMMA and "SaltA (m=7.2)" were mixed with PMMA:"SaltA (m=7.2)"=30:70 by mass.

Moreover, "PMMA10+SaltA (m=7.2)" and "PMMA20+SaltA (m=7.2)" were prepared in the same manner. In "PMMA10+SaltA (m=7.2)," PMMA and "SaltA (m=7.2)" were mixed with PMMA:"SaltA (m=7.2)"=10:90 by mass. In "PMMA20+SaltA (m=7.2)," PMMA and "SaltA (m=7.2)" were mixed with PMMA:"SaltA (m=7.2)"=20:80 by mass.

Figure 6:
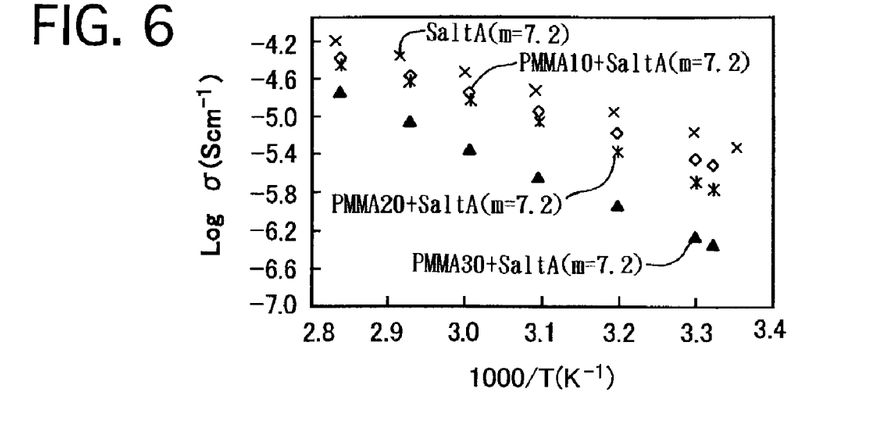
FIG. 6 is a graph for illustrating the temperature dependencies of the ionic conductivities exhibited by respective test samples in Example No. 5.

FIG. 6 illustrates the relationships between the contents of PMMA and the ionic conductivities concerning the ionic conductors of "PMMA+SaltA (m=7.2)" system.

It is apparent from FIG. 6 that the ionic conductivities were lowered by increasing the PMMA addition amount. When PMMA was added in an amount of 30% by mass, the film strength became considerably good.

Example No. 6

Preparation of Ionic Conductors Comprising Vinylidene Fluoride (PVdF)-Hexafluoropropylene (HFP) Copolymer and "SaltA" and Measurement on Ionic Conductivity 0.1922 g PVdF-HFP and 0.4485 g "SaltA (m=7.2)" were dissolved in 20 mL acetone. The mixture was stirred for 12 hours. Thereafter, the solvent was distilled out by depressurizing, and the reactant was further dried at 70° C. by depressurizing for 24 hours. Thus, a yellow ionic conductor was prepared, and was labeled as "PVdF-HFP30+SaltA (m=7.2)." In "PVdF-HFP30+SaltA (m=7.2)," PVdF-HFP and "SaltA (m=7.2)" were mixed with PVdF-HFP "SaltA (m=7.2)"=30:70 by mass.

Moreover, "PVdF-HFP10+SaltA (m=7.2)" and "PVdF-HFP20+SaltA (m=7.2)" were prepared in the same manner. In "PVdF-HFP10+SaltA (m=7.2)," PVdF-HFP and "SaltA (m=7.2)" were mixed with PVdF:"SaltA (m=7.2)"=10:90 by mass. In "PVdF-HFP20+SaltA (m=7.2)," PVdF-HFP and "SaltA (m=7.2)" were mixed with PMMA:"SaltA (m=7.2)"=20:80 by mass.

Figure 7:
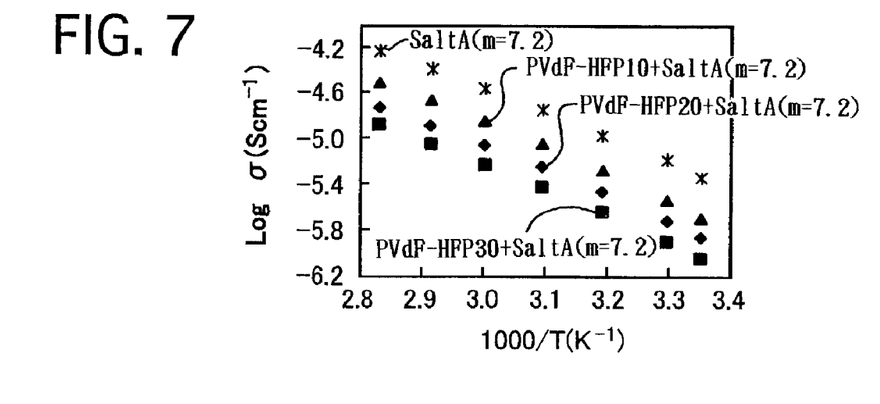
FIG. 7 is a graph for illustrating the temperature dependencies of the ionic conductivities exhibited by respective test samples in Example No. 6.

FIG. 7 illustrates the relationships between the contents of PVdF-HFP and the ionic conductivities concerning the ionic conductors of "PVdF-HFP+SaltA (m=7.2) system.

The following are apparent from FIG. 7. Similarly to the case where PMMA was used, when PVdF-HFP was used as well, it was seen that the ionic conductivities were lowered as the content of PVdF-HFP was increased. When PVdF-HFP was added in an amount of 30% by mass, the film strength was improved considerably, but was slightly inferior to that of the ionic conductors in which PMMA was added.

Example No. 7

Preparation of Ionic Conductors Comprising Polyethylene Oxide (PEO), "SaltA (m=7.2)" and $BaTiO_3$ being Filler and Measurement on Ionic Conductivity 0.0300 g PEO, 0.1797 g "SaltA (m=7.2)" and 0.00105 g $BaTiO_3$ were dissolved in 15 mL acetonitrile. The mixture was stirred for 12 hours. Thereafter, the solvent was distilled out by depressurizing, and the reactant was further dried at 70° C. by depressurizing for 24 hours. Thus, a white ionic conductor was prepared, and was labeled as "PEO+BaTiO$_3$5." In "PEO+BaTiO$_3$5," the ratio (O/Li) by number of atoms, i.e., the sum of the number of oxygen atoms, resulting from the oligoethylene oxide group, and ethereal oxygen atoms, included the structural member, with respect to the number of lithium ions, included in the lithium salt, was 20/1, and a ratio {(PEO+"SaltA (m=7.2)")/BaTiO$_3$}, i.e., the sum of PEO and "SaltA (m=7.2)" with respect to BaTiO$_3$, was (PEO+"SaltA (m=7.2)"):BaTiO$_3$=95:5 by mass.

Moreover, "PEO+BaTiO$_3$10" was prepared in the same manner. In "PEO+BaTiO$_3$10", the ratio (O/Li) was 20/1, and the ratio {(PEO+"SaltA (m=7.2")")/BaTiO$_3$} was 90/10 by mass.

Figure 8:
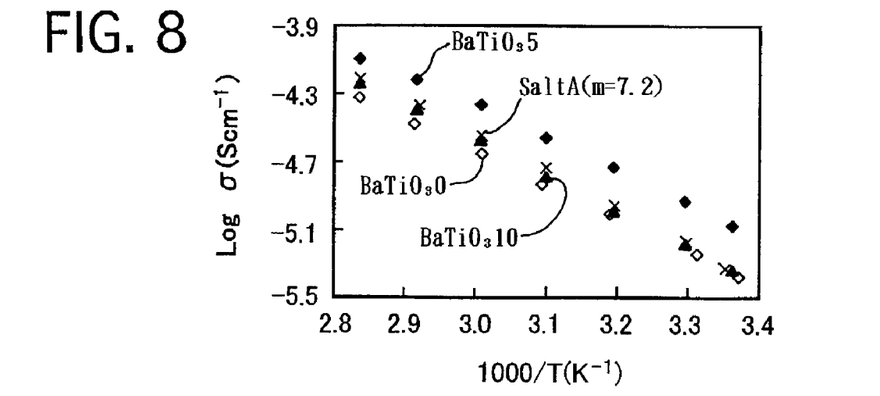
FIG. 8 is a graph for illustrating the temperature dependencies of the ionic conductivities exhibited by respective test samples in Example No. 7.

FIG. 8 illustrates the relationships between the BaTiO$_3$ contents and the ionic conductivities concerning the ionic conductors of "PEO+SaltA (m=7.2)" system.

It is apparent from FIG. 8 that the ionic conductivities were improved by adding BaTiO$_3$ to the ionic conductors of "PEO+SaltA (m=7.2)" system. When BaTiO$_3$ was added in an amount of 5% by mass, the ionic conductor of "PEO+SaltA (m=7.2)" system exhibited the maximum ionic conductivities. The film strength was also improved by adding BaTiO$_3$.

Note that the BaTiO$_3$ addition effect was observed in the ionic conductors of "PMMA+SaltA (m=7.2)" system as well, though the results will not be described in detail herein.

Example No. 8

Measurement on Ionic Conductivity of Liquid Electrolyte

Figure 9:
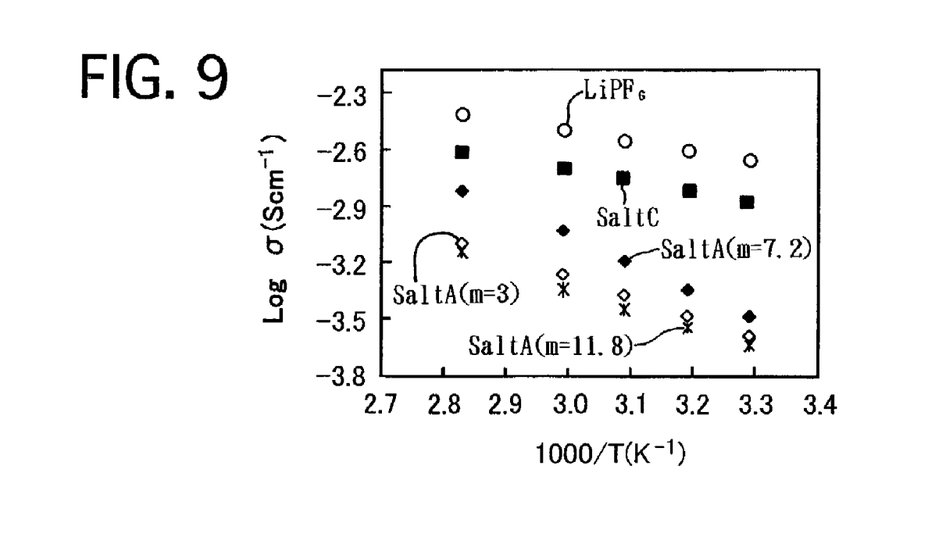
FIG. 9 is a graph for illustrating the temperature dependencies of the ionic conductivities exhibited by respective test samples in Example No. 8.
Figure 10:
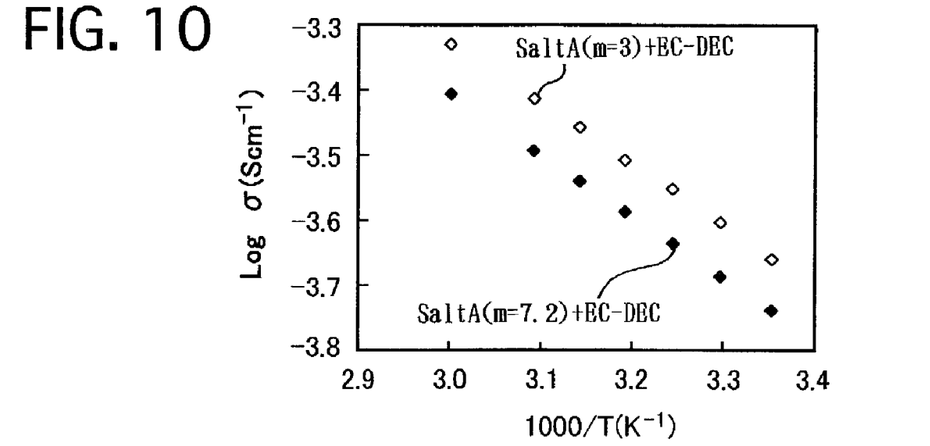
FIG. 10 is a graph for illustrating the temperature dependencies of the ionic conductivities exhibited by respective test samples in Example No. 8.

A mixture of ethylene carbonate (EC) and propylene carbonate (PC) was used as a solvent in which EC and PC were mixed with a ratio of EC:PC=50:50 by volume. Liquid electrolytes were prepared in which each of "SaltA (m=3)," "SaltA (m=7.2)" and "SaltA (m=11.8)" was dissolved in EC-PC in a concentration of 0.1M. The ion conductivities of the resulting liquid electrolytes were compared to those of $LiPF_6$ and "SaltC." FIG. 9 illustrates the results. Moreover, a mixture of EC and diethyl carbonate (DEC) was used as a solvent in which EC and DEC were mixed with a ratio of EC:DEC=50:50 by volume. Liquid electrolytes were prepared in which each of "SaltA (m=3)" and "SaltA (m=7.2)" was dissolved in EC-DEC in a concentration of 1M. FIG. 10 illustrates the ion conductivities of the resulting liquid electrolytes. Note that FIG. 9 also illustrates the ionic conductivities of a liquid electrolyte in which $LiPF_6$ was dissolved in EC-PC in a concentration of 1M for reference.

It is apparent from FIG. 9 that "SaltC," which was prepared by substituting $CF_3COO$— groups, being an electrophilic substituent group, for all of the hydrogen atoms of $LiAlH_4$ exhibited higher ionic conductivities. On the contrary, the liquid electrolyte of "SaltA" system which had ether chains exhibited lower ionic conductivity values. The reasons are believed as follows. The causes were that the dissociation of "SaltC" was high; and that "SaltA" was viscous liquid with large molecular weight so that the viscosity of the liquid electrolyte was heightened.

Moreover, in the liquid electrolytes of "EO-DEC+SaltA" system as well, the ionic conductivities of the liquid electrolyte with "SaltA (m=7.2)" dissolved were lower than those of the liquid electrolyte with "SaltA (m=3)" dissolved. The reason is believed that the viscosity of the former liquid electrolyte was higher.

Example No. 9

Ionic conductors were prepared by using "SaltA (m=7.2)" according to the present invention, "SaltC," and LiTFSI and LiTrif, which have been used conventionally, as the lithium salt. Note that PEO was used as the structural member, and that the ratio (O/Li) was controlled at 20/1 in all of them. The ionic conductivities of the resulting ionic conductors were measured.

Figure 11:
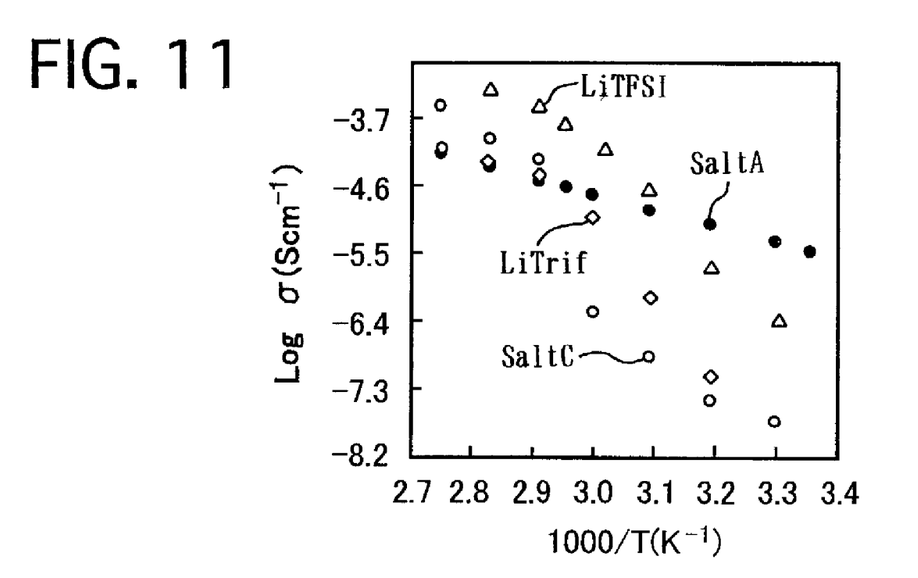
FIG. 11 is a graph for illustrating the temperature dependencies of the ionic conductivities exhibited by respective test samples in Example No. 9.

FIG. 11 illustrates the results. The ionic conductor comprising PEO and "SaltA" exhibited lower ionic conductivities at high temperatures than the ionic conductors comprising the conventional lithium salts did. However, the ionic conductivities of the ionic conductor comprising PEO and "SaltA" were lowered least at low temperatures. Thus, the ionic conductor comprising PEO and "SaltA" could maintain high ionic conductivities at low temperatures. On the other hand, the ionic conductor comprising PEO and "SaltC" exhibited a low ionic conductivity at room temperature, but exhibited high ionic conductivities at relatively high temperatures around 70° C.

Having now fully described the present invention, it will be apparent to one of ordinary skill in the art that many changes and modifications can be made thereto without departing from the spirit or scope of the present invention as set forth herein including the appended claims.

What is claimed is:

1. A lithium salt expressed by a formula below:
    $LiAlX_n(OY)_{4-n}$, where "X" is at least one member selected from the group consisting of $RCO_2$—, $RSO_3$—, and $(RSO_2)_2N$—, where "R" is at least one member selected from the group consisting of an alkyl group and a perflouroalkyl group and "Y" is an oligoether group and n is 1, 2 or 3.

2. The lithium salt set forth in claim 1, wherein "n" is 2 in said formula.

3. The lithium salt set forth in claim 1, wherein said "Y" is $CH_3(OCH_2CH_2)_m$— where "m"$\geq 1$.

4. The lithium salt set forth in claim 1, wherein a ratio (O/Li) of the number of oxygen atoms, included in said "Y" of said formula, with respect to the number of lithium ions, included therein, falls in a range of from 2/1 to 90/1.

5. The lithium salt set forth in claim 1 being liquid at room temperature.

6. An ionic conductor, comprising:
    a structural member; and
    a lithium salt dispersed in the structural member, and expressed by a formula below:
    $LiAlX_n(OY)_{4-n}$, where "X" is at least one member selected from the group consisting of $RCO_2$—, $RSO_3$—, and $(RSO_2)_2N$—, where "R" is at least one member selected from the group consisting of an alkyl group and a perflouroalkyl group and "Y" is an oligoether group and n is 1, 2 or 3.

7. The ionic conductor set forth in claim 6, wherein said structural member is at least one member selected from the group consisting of polyethylene oxide, ethylene oxide-propylene oxide copolymers, poly(methoxyoligoethyleneglycoxy) methacrylate, polymethyl methacrylate, polyethyl methacrylate, polybutyl methacrylate, polyvinylidene fluoride, and vinylidene fluoride-hexafluoropropylene copolymers.

8. The ionic conductor set forth in claim 6 further including barium titanate ($BaTiO_3$).

9. The ionic conductor set forth in claim 6, wherein a ratio (O/Li) of the sum of the number of oxygen atoms, included in said "Y" of said lithium salt, and ethereal oxygen atoms of said structural member, with respect to the number of lithium ions, included in said lithium salt, falls in a range of from 6/1 to 100/1.

10. A liquid electrolyte, comprising:
    a solvent; and
    a lithium salt dissolved in the solvent, and expressed by a formula below:
    $LiAlX_n(OY)_{4-n}$, where "X" is at least one member selected from the group consisting of $RCO_2$—, $RSO_3$—, and $(RSO_2)_2N$—, where "R" is at least one member selected from the group consisting of an alkyl group and a perflouroalkyl group and "Y" is an oligoether group and n is 1, 2 or 3.

11. The liquid electrolyte set forth in claim 10, wherein said solvent is at least one member selected from the group consisting of ethylene carbonate, propylene carbonate, diethyl carbonate, dimethyl carbonate, γ-butyrolactone, diethylene glycol dimethylether, and ethylene glycol dimethylether.

12. An ionic conductor, comprising:

a structural member being at least one member selected from the group consisting of polyethylene oxide, ethylene oxide-propylene oxide copolymers, poly(methoxyoligoethyleneglycoxy) methacrylate, polymethyl methacrylate, polyethyl methacrylate, polybutyl methacrylate, polyvinylidene fluoride, and vinylidene fluoride-hexafluoropropylene copolymers; and a lithium salt dispersed in the structural member, and expressed by a formula below:

$LiAlX_n(OY)_{4-n}$, where "X" is an electron attracting group and "Y" is an oligoether group and n is 1, 2 or 3.

* * * * *